US012188108B2

(12) United States Patent
Griebel et al.

(10) Patent No.: US 12,188,108 B2
(45) Date of Patent: Jan. 7, 2025

(54) MAGNESIUM-BASED ABSORBABLE ALLOYS

(71) Applicant: Fort Wayne Metals Research Products Corp, Fort Wayne, IN (US)

(72) Inventors: Adam J. Griebel, Fort Wayne, IN (US); Jeremy E. Schaffer, Fort Wayne, IN (US)

(73) Assignee: Fort Wayne Metals Research Products LLC, Fort Wayne, IN (US)

( * ) Notice: Subject to any disclaimer, the term of this patent is extended or adjusted under 35 U.S.C. 154(b) by 472 days.

(21) Appl. No.: 17/616,132

(22) PCT Filed: Jun. 2, 2020

(86) PCT No.: PCT/US2020/035731
§ 371 (c)(1),
(2) Date: Dec. 2, 2021

(87) PCT Pub. No.: WO2020/247383
PCT Pub. Date: Dec. 10, 2020

(65) Prior Publication Data
US 2022/0251688 A1 Aug. 11, 2022

(51) Int. Cl.
C22C 23/00 (2006.01)
A61F 2/90 (2013.01)
A61L 31/02 (2006.01)
A61L 31/14 (2006.01)

(52) U.S. Cl.
CPC ............... *C22C 23/00* (2013.01); *A61F 2/90* (2013.01); *A61L 31/022* (2013.01); *A61L 31/148* (2013.01); *A61L 2300/604* (2013.01)

(58) Field of Classification Search
CPC ............ C22C 23/00; C22C 23/04; C22F 1/06
See application file for complete search history.

(56) References Cited

U.S. PATENT DOCUMENTS

| | | |
|---|---|---|
| 1,919,361 A | 7/1933 | Farrington |
| 3,320,055 A | 5/1967 | Foerster |
| 6,471,797 B1 | 10/2002 | Kim et al. |
| 7,942,986 B2 | 5/2011 | Bettles et al. |
| 8,034,101 B2 | 10/2011 | Yamamoto et al. |
| 8,293,031 B2 | 10/2012 | Gerold et al. |
| 8,414,717 B2 | 4/2013 | Buha |
| 8,425,835 B2 | 4/2013 | Harder et al. |
| 8,435,281 B2 | 5/2013 | Weber |
| 8,815,148 B2 | 8/2014 | Popowski et al. |
| 8,986,369 B2 | 3/2015 | Steckel et al. |
| 9,074,269 B2 | 7/2015 | Gerold et al. |
| 9,402,669 B2 | 8/2016 | Neubert et al. |
| 9,523,141 B2 | 12/2016 | Washio et al. |
| 9,593,397 B2 | 3/2017 | Imwinkelried et al. |
| 9,603,728 B2 | 3/2017 | Stinson et al. |
| 9,757,174 B2 | 9/2017 | Weinberg |
| 9,757,796 B2 | 9/2017 | Sherman et al. |
| 9,775,647 B2 | 10/2017 | Schiffl et al. |
| 9,943,625 B2 | 4/2018 | Koo et al. |
| 10,022,470 B2 | 7/2018 | Decker et al. |
| 10,052,188 B2 | 8/2018 | Kalb et al. |
| 10,085,860 B2 | 10/2018 | Steckel et al. |
| 10,184,165 B2 | 1/2019 | Kawamura et al. |
| 10,196,715 B2 | 2/2019 | Imwinkelried et al. |
| 10,202,672 B2 | 2/2019 | Yuichi |
| 10,322,214 B2 | 6/2019 | Pulugurtha et al. |
| 10,358,709 B2 | 7/2019 | Mueller et al. |
| 10,478,529 B2 | 11/2019 | Imwinkelried et al. |
| 10,570,490 B2 | 2/2020 | Nie et al. |
| 10,589,005 B2 | 3/2020 | Edick et al. |
| 10,752,981 B2 | 8/2020 | Miura |
| 10,767,248 B2 | 9/2020 | Lee et al. |
| 10,842,911 B2 | 11/2020 | Ueda et al. |
| 10,954,587 B2 | 3/2021 | Mueller et al. |
| 10,994,056 B2 | 5/2021 | Mukai et al. |
| 11,040,126 B2 | 6/2021 | Ma et al. |
| 11,077,227 B2 | 8/2021 | Kumta et al. |
| 11,085,105 B2 | 8/2021 | Zheng et al. |
| 2002/0004060 A1 | 1/2002 | Heublein et al. |
| 2003/0029526 A1 | 2/2003 | Kim et al. |
| 2004/0241036 A1 | 12/2004 | Meyer-Lindenberg et al. |
| 2005/0139466 A1 | 6/2005 | Morris |
| 2006/0018954 A1 | 1/2006 | Kuttler |
| 2006/0065332 A1 | 3/2006 | Ienaga et al. |

(Continued)

FOREIGN PATENT DOCUMENTS

| | | |
|---|---|---|
| EP | 1959025 A1 | 8/2008 |
| EP | 2582408 A2 | 4/2013 |

(Continued)

OTHER PUBLICATIONS

Hofstetter Joëlle., Development of high-strength low-alloy (HSLA) magnesium alloys for biomedical application, Doctor of Sciences of Eth Zurich, Diss. ETH No. 22685, 2015, 154 pages.

(Continued)

*Primary Examiner* — Jessee R Roe
(74) *Attorney, Agent, or Firm* — Faegre Drinker Biddle & Reath LLP

(57) ABSTRACT

A magnesium alloy contains a small amount of lithium, zinc, calcium, and manganese. For example, the magnesium alloy may include between 1-5 wt. % lithium, between 0.2-2.0 wt. % zinc, between 0.1-0.5 wt. % calcium, and between 0.1-0.8 wt. % manganese. These alloying elements are all nutrient elements, such that the present alloy can be safely broken down in vivo, then absorbed and/or expelled from the body. Li, Zn, Ca and Mn each contribute to solid-solution strengthening of the alloy. Ca also acts as a grain refiner, while Zn and Ca both form strengthening and corrosion-controlling intermetallic compounds. Optionally, the alloy may also include a small amount of yttrium for added strength and corrosion resistance.

23 Claims, 9 Drawing Sheets

(56) References Cited

U.S. PATENT DOCUMENTS

| | | |
|---|---|---|
| 2006/0198869 A1 | 9/2006 | Furst et al. |
| 2008/0140199 A1 | 6/2008 | Briest |
| 2008/0317621 A1 | 12/2008 | Aoki et al. |
| 2009/0081313 A1 | 3/2009 | Aghion et al. |
| 2009/0306725 A1 | 12/2009 | Hiromoto et al. |
| 2009/0317622 A1 | 12/2009 | Huang et al. |
| 2010/0075162 A1 | 3/2010 | Yang et al. |
| 2010/0310409 A1 | 12/2010 | Gibson et al. |
| 2011/0076319 A1 | 3/2011 | Orlowski et al. |
| 2011/0183156 A1 | 7/2011 | Song |
| 2011/0251669 A1 | 10/2011 | Heublein et al. |
| 2012/0070248 A1 | 3/2012 | Kuwabara et al. |
| 2012/0143227 A1 | 6/2012 | Steckel et al. |
| 2012/0195787 A1 | 8/2012 | Huang et al. |
| 2013/0018480 A1 | 1/2013 | Kopp |
| 2013/0090741 A1 | 4/2013 | Guo et al. |
| 2013/0131814 A1 | 5/2013 | Koo et al. |
| 2013/0209195 A1 | 8/2013 | Kuwabara et al. |
| 2015/0064053 A1 | 3/2015 | Washio et al. |
| 2015/0083285 A1 | 3/2015 | Somekawa et al. |
| 2015/0167128 A1 | 6/2015 | Fine et al. |
| 2016/0068933 A1 | 3/2016 | Kawamura et al. |
| 2016/0138148 A1 | 5/2016 | Schaffer et al. |
| 2016/0304996 A1 | 10/2016 | Bronfin et al. |
| 2017/0002459 A1 | 1/2017 | Lenczowski et al. |
| 2017/0266346 A1 | 9/2017 | Kumta et al. |
| 2018/0036456 A1 | 2/2018 | Shin |
| 2019/0001027 A1 | 1/2019 | Ibrahim et al. |
| 2019/0085433 A1 | 3/2019 | Sung et al. |
| 2019/0153570 A1 | 5/2019 | Zhou et al. |
| 2019/0177819 A1 | 6/2019 | Kim et al. |
| 2019/0249286 A1 | 8/2019 | Kim et al. |
| 2019/0298890 A1 | 10/2019 | Pulugurtha et al. |
| 2019/0330718 A1 | 10/2019 | Ueda et al. |
| 2020/0056270 A1 | 2/2020 | Kim et al. |
| 2020/0063242 A1 | 2/2020 | Valls Anglés |
| 2020/0123636 A1 | 4/2020 | Eliezer et al. |
| 2020/0173000 A1 | 6/2020 | Koo et al. |
| 2020/0376172 A1 | 12/2020 | Bow et al. |
| 2020/0384160 A1 | 12/2020 | Decker et al. |
| 2021/0137709 A1 | 5/2021 | Stinson et al. |

FOREIGN PATENT DOCUMENTS

| | | | |
|---|---|---|---|
| EP | 2678047 A1 | 1/2014 | |
| JP | 2001-511049 | 8/2001 | |
| WO | 2011/163236 A2 | 12/2011 | |
| WO | 2012/113624 A1 | 8/2012 | |
| WO | WO-2014197781 A2 * | 12/2014 | ........... A61L 31/022 |
| WO | 2018/079923 A1 | 5/2018 | |
| WO | 2018/154124 A1 | 8/2018 | |
| WO | 2019/002277 A1 | 1/2019 | |
| WO | 2019/043394 A1 | 3/2019 | |
| WO | 2020/104653 A1 | 5/2020 | |
| WO | 2020/111854 A1 | 6/2020 | |
| WO | 2020/203980 A1 | 10/2020 | |
| WO | 2021/040988 A1 | 3/2021 | |
| WO | 2021/112764 A1 | 6/2021 | |
| WO | 2021/131205 A1 | 7/2021 | |

OTHER PUBLICATIONS

International Preliminary Report on Patentability received for PCT Patent Application No. PCT/US2020/035731, mailed on Dec. 16, 2021, 8 pages.

International Search Report and Written Opinion received for PCT Patent Application No. PCT/US2020/035731, mailed on Sep. 8, 2020, 8 pages.

Witte et al., "In vivo corrosion and corrosion protection of magnesium alloy LAE442", Acta Biomater, vol. 6 No. 5, 2010, pp. 1792-1799.

* cited by examiner

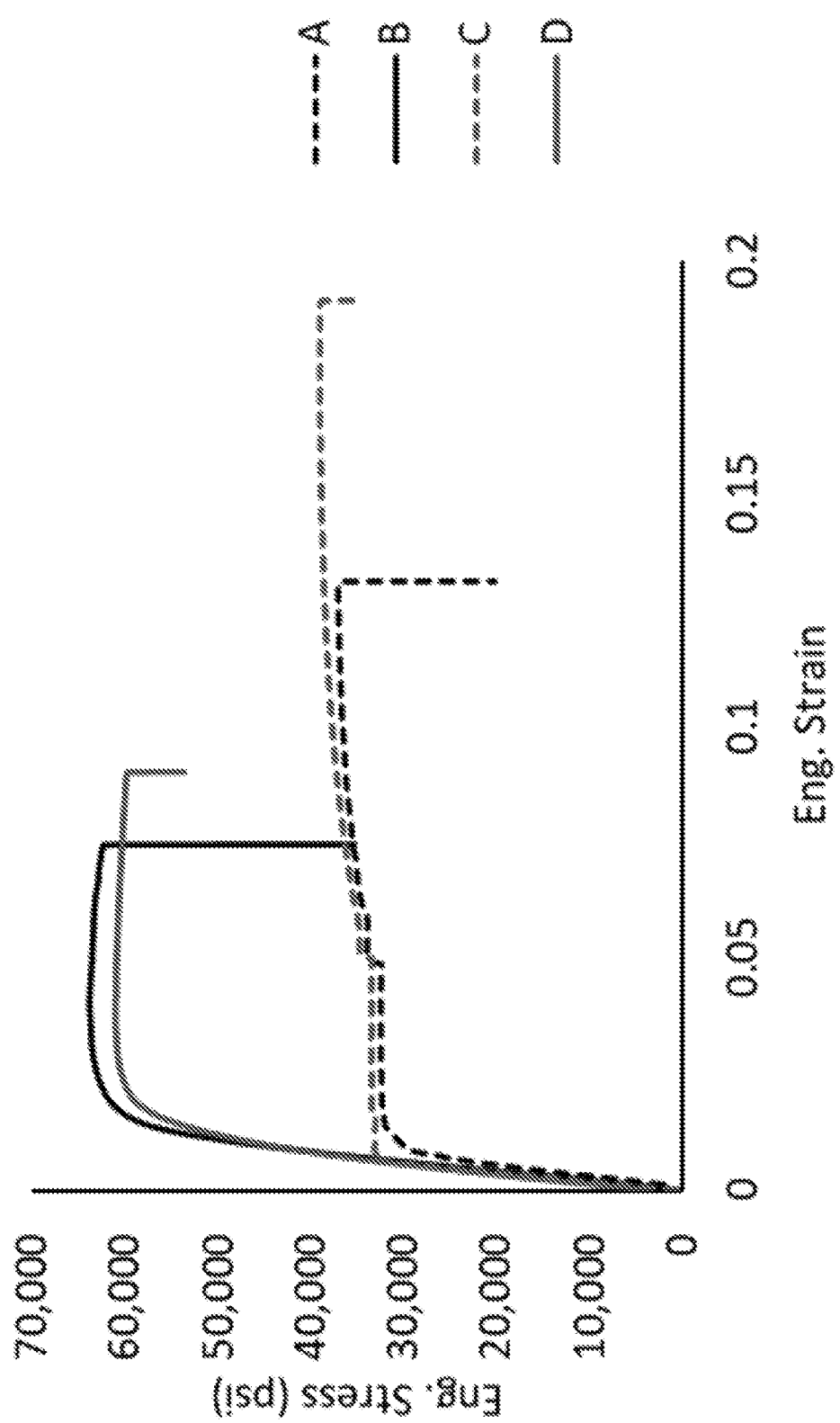

MAGNESIUM-BASED ABSORBABLE ALLOYS

CROSS-REFERENCE TO RELATED APPLICATIONS

The present application is a U.S. national phase application under 35 U.S.C. § 371 of International Application No. PCT/US2020/035731, filed Jun. 2, 2020, titled MAGNESIUM-BASED ABSORBABLE ALLOYS, which claims the benefit of U.S. Provisional Patent Application No. 62/856,293 filed Jun. 3, 2019 and entitled MAGNESIUM-BASED ABSORBABLE ALLOYS, the entire disclosures of which is are hereby expressly incorporated herein by reference.

BACKGROUND

1. Technical Field

The present invention relates to wire used in biomedical applications and, in particular, relates to a biodegradable wire for use in medical devices such as stents.

2. Description of the Related Art

Specialized absorbable materials are a focus of ongoing development for surgical implant applications. For example, design efforts for creating absorbable stents have focused primarily on balloon-expandable technology for coronary pathologies, and may include polymeric materials such as poly-L lactic acid (PLLA) or poly-L glycolic acid (PLGA), or metallic materials such as magnesium (Mg), iron (Fe), or zinc (Zn) based alloys. Some research methods have also focused on hybrids including various combinations of absorbable polymers and metals. While such materials are absorbable, their functional properties, such as mechanical strength and ductility, corrosion rate, or biocompatibility, may not be adequate for a particular application.

Other applications for absorbable materials, including nutrient metal absorbable materials, include temporary fracture fixation devices such as bone plates. In some instances, it is necessary for a bone plate to provide a designated level of mechanical strength during bone regrowth following a fracture, but the plate's presence after fracture healing may cause complications and/or require surgical removal.

Many magnesium-based alloys have been investigated for their utility in such absorbable implant applications. WE43, for example, is an alloy containing nominally 4 wt. % Y and 3 wt. % other rare earths (predominantly Nd) and 0.5% Zr. This alloy has relatively high strength, moderate ductility, and a generally acceptable corrosion rate. It does, however, have a relatively high amount of rare earth elements which may have long residence times in the body.

Other magnesium-based alloys have been investigated which are free of rare earth elements, instead comprising additions elements native to the body, like Zn, Ca, and/or Mn. These alloys generally have less strength than the rare-earth-containing alloys, coupled with comparable ductility. Their corrosion rates are adjustable based on specific precipitates formed through heat treatment. These alloys may not have sufficient strength for certain applications, such as wire-based medical devices.

In addition, the ductility of known rare-earth and magnesium-based alloys described above is only moderate, and for some devices requiring significant plastic deformation (e.g. staples, clips, or stents), more ductility is desirable. More ductility also improves the manufacturability of semi-finished products for such devices.

It is known that addition of lithium (Li) to Mg will improve the alloy's ductility. At greater than 11 wt. % Li, the crystal structure of the alloy changes from the brittle hexagonal-close-packed (HCP) to the ductile body-centered-cubic (BCC). Between about 6 wt. % to about 11 wt. %, a biphasic structure of both HCP and BCC exists, and below 6 wt. % Li, the native HCP is retained. Mg—Li binary alloys, Mg—Li—Ca alloys, and Mg—Li—Al-Rare Earth alloys have been investigated as potential absorbable metals. While Li has been found to increase ductility, it also decreases strength and may reduce the corrosion rate. It is also a psychoactive element, and large amounts of Li in an alloy may have related adverse effects.

Known absorbable magnesium-based alloys therefore have various combinations of strength, ductility, biocompatibility, and corrosion resistance. However, none of the known absorbable alloys have the optimal combination of these parameters for devices requiring significant plastic deformation.

What is needed is an improvement over the foregoing.

SUMMARY

The present disclosure is directed to a magnesium alloy containing a small amount of lithium, zinc, calcium, and manganese. For example, the magnesium alloy may include between 1-5 wt. % lithium, between 0.2-2.0 wt. % zinc, between 0.1-0.5 wt. % calcium, and between 0.1-0.8 wt. % manganese. These alloying elements are all nutrient elements, such that the present alloy can be safely broken down in vivo, then absorbed and/or expelled from the body. Li, Zn, Ca and Mn each contribute to solid-solution strengthening of the alloy. Ca also acts as a grain refiner, while Zn and Ca both form strengthening and corrosion-controlling intermetallic compounds. Optionally, the alloy may also include a small amount of yttrium for added strength and corrosion resistance.

In one form thereof, the present disclosure provides an alloy for use in an absorbable medical device, the alloy comprising between 1.0-5.0 wt. % lithium, between 0.2-2.0 wt. % zinc, between 0.1-0.5 wt. % calcium, between 0.1-0.8 wt. % manganese, and balance magnesium and inevitable impurities.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein:

FIG. 6B is a stress-strain graph, drawn to scale, showing additional characteristics of material made in accordance with the present disclosure;

Figure 1:
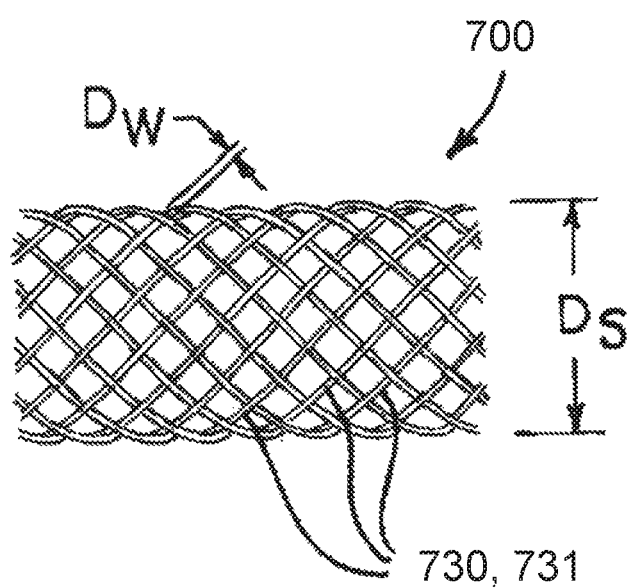
FIG. 1 is an elevation view illustrating the geometry of a braided stent having diameter Ds, the stent comprising wire elements formed into a mesh tubular scaffold, in accordance with the present disclosure.

Corresponding reference characters indicate corresponding parts throughout the several views. Although the exemplifications set out herein illustrate embodiments of the invention, the embodiments disclosed below are not intended to be exhaustive or to be construed as limiting the scope of the invention to the precise form disclosed.

DETAILED DESCRIPTION

1. Introduction

The alloy of the present disclosure is a magnesium-lithium-zinc-calcium-manganese (Mg—Li—Zn—Ca—Mn) alloy that exhibits an absorbable alloy which exhibits a combination of high ductility and workability, high strength and a suitable in vivo degradation profile. Yttrium may also be included for some applications, particularly where increases in strength and/or corrosion resistance are desired.

2. Terminology

As used herein, "wire" or "wire product" encompasses continuous wire and wire products which may be continuously produced and wound onto a spool for later dispensation and use, such as wire having a round cross section and wire having a non-round cross section, including flat wire or ribbon. "Wire" or "wire product" also encompasses other wire-based products such as strands, cables, coil, and tubing, which may be produced at a particular length depending on a particular application. In some exemplary embodiments, a wire or wire product in accordance with the present disclosure may have a diameter up to 2.5 mm. In addition to wire and wire products, the principles of the present disclosure can be used to manufacture other material forms such as rod materials having a diameter greater than 2.5 mm up to 20 mm. Thin material sheets may also be made. Exemplary tubing structures may be in wire form or rod form, with inside diameters ranging from 0.5 mm to 4.0 mm, and wall thicknesses ranging from 0.100 mm to 1.00 mm. "Fine wire" refers to a wire having an outer diameter of less than 1 mm.

As used herein, "fatigue strength" refers to the load level at which the material meets or exceeds a given number of load cycles to failure. Herein, the load level is given as alternating strain, as is standard for displacement or strain-controlled fatigue testing, whereby terms are in agreement with those given in ASTM E606, the entirety of which is incorporated herein by reference.

"DFT®" is a registered trademark of Fort Wayne Metals Research Products Corp. of Fort Wayne, IN, and refers to a bimetal or poly-metal composite wire product including two or more concentric layers of metals or alloys, typically at least one outer layer disposed over a core filament formed by drawing a tube or multiple tube layers over a solid metallic wire core element.

"Impurities," "incidental impurities" and "trace impurities" are material constituents present in a material at less than 500 parts per million or 0.05 wt. % for any given element.

3. Magnesium Alloy

The present magnesium-based alloy may include between 1-5 wt. % lithium, between 0.2-2.0 wt. % zinc, between 0.1-0.5 wt. % calcium, and between 0.1-0.8 wt. % manganese, with the balance magnesium and inevitable impurities. For some applications, yttrium may also be added in an amount up to 2.5 wt. %. All other elements are excluded from the present alloy, such that magnesium represents at least 89 wt. %, and up to 98.6 wt. % of the total alloy.

These alloys have been found to provide a magnesium-based alloy which exhibits both high ductility and high strength, while using only elements either native to the human body or easily processed by the human body. As described in further detail below, this combination of material properties provides an absorbable alloy with predictable and suitable in vivo degradation profile, but which can also be efficiently produced in large volume.

As further described below, the present Mg—Li—Zn—Ca—Mn material exhibits high ductility. This ductility facilitates fabrication and processing of they alloy, because it allows for larger amounts of cold work and therefore can be reduced to a desired diameter with fewer iterations of cold drawing and annealing, and with lower energy required for effecting cold work. The high ductility of the present material also broadens the scope of potential medical device applications by inhibiting the potential for breakage, especially in devices requiring high levels of compression strain like stents, staples, or ligation clips.

The present Mg—Li—Zn—Ca—Mn material also exhibits relatively high strength, which can be enhanced by cold working to a desired level. This high strength also facilitates use of the alloy in certain medical devices. For example, strength may be needed for vascular vessel support in a stent application, or for bone support in an orthopedic or orthodontic device application.

The present alloy also performs corrodes predictably and favorably in an in vivo environment.

Lithium is included to improve the ductility of the present Mg-based alloy, while also being easily and safely processed by the body. Lithium is a nutrient metal, with a typical suggested daily dietary intake of 1 mg. Thus, a relatively large amount of lithium can be included as a part of wires 730 or 731 or other materials made in accordance with the present disclosure without adverse effect. Lithium of at least 1.0 wt. % is needed to produce the desired increase in ductility, but lithium in excess of 5.0 wt. % results in a loss of strength, potential for an increased corrosion rate, and an unnecessarily high dose of lithium to the body.

Zinc is included as a contributor to solid-solution strengthening of the alloy, and it can also form intermetallic compounds in the present material which serve to mediate and control corrosion. In particular, when zinc is present together with calcium in a desired amount, and after certain heat treatments, the zinc may contribute to formation of $Mg_6Zn_3Ca_2$ intermetallic compounds which are more noble than the base metal, and may increase the rate of corrosion. Zinc is a nutrient metal easily and safely processed by the body such that a relatively large amount can be included as a part of wires 730 or 731 or other materials made in accordance with the present disclosure without adverse effect. Zinc of at least 0.2 wt. % is needed to produce the desired increase in strength, but zinc in excess of 2.0 wt. % results in excessive $Mg_6Zn_3Ca_2$ formation which can lead to a corrosion rate which is too high for most applications.

Calcium is included as another contributor to solid-solution strengthening of the alloy, which can also form intermetallic compounds in the present material which serve to mediate and control corrosion. $Mg_2Ca$ is less noble than the base metal, and will reduce bulk corrosion by acting as a microgalvanic sacrificial anodes. As mentioned previously, the $Mg_6Zn_3Ca_2$ phase can help to increase bulk corrosion, so calcium enables some amount of control of the corrosion rate of the Mg alloy. Calcium is also a grain refiner which contributes to strength, ductility and workability of the finished material. Like zinc, calcium is a nutrient metal easily and safely processed by the body such that a relatively large amount can be included as a part of wires 730 or 731 or other materials made in accordance with the present disclosure without adverse effect. Calcium of at least 0.1 wt. % is needed to produce the desired increase in strength, but calcium in excess of 0.5 wt. % results in excessive formation of $Mg_2Ca$ phases at the grain boundaries, which can decrease ductility and workability.

Manganese is included as yet another contributor to solid-solution strengthening of the alloy. Manganese is able to reduce the harmful effects of iron impurities in the material on the corrosion behavior of the alloy. Manganese is also a nutrient metal that is easily and safely processed by the body such that a relatively large amount can be included as a part of wires 730 or 731 or other materials made in accordance with the present disclosure without adverse effect. Manganese of at least 0.1 wt. % is needed to produce the desired increase in strength, but manganese in excess of 0.8 wt. % results in excessive precipitation of alpha-Mn particles, which can negatively impact corrosion resistance.

Yttrium may also be optionally added to the present Mg—Li—Zn—Ca—Mn alloy. Yttrium is a rare earth element known to be well-tolerated by the body. Yttrium (or its salts) have a relatively high aqueous solubility, meaning it is more easily processed by the body than some other rare earths. The addition of yttrium may increase both strength through solid-solution strengthening and ductility through texture reduction and grain refinement. However, yttrium in excess of 2.5 wt. % results in decreased ductility and more Y-containing intermetallic particles which may have a relatively long residence time in vivo.

The foregoing elements are an exhaustive list of the materials used in connection with the present magnesium-based material. Other elements are specifically excluded, except for the presence of inevitable impurities as described above.

4. Wire Constructs Including Mg—Li—Zn—Ca—Mn—(Y)

In one exemplary embodiment, Mg—Li—Zn—Ca—Mn material made in accordance with the present disclosure may be formed into a fine medical-grade wire 730, 731, as shown in FIG. 1. This wire 730, 731 may then be formed or integrated into a medical device, such as by braiding into a stent 700 having an overall device diameter Ds (FIG. 1) Wires 730, 731 may each have an outer wire diameter Dw of less than, e.g., 1 mm.

An alloy in accordance with the present disclosure may first be formed in bulk, such as by traditional casting methods. This bulk material is then formed into a suitable pre-form material (e.g., a rod, plate or hollow tube) by hot-working the bulk material into the desired pre-form size and shape. For purposes of the present disclosure, hot working is accomplished by heating the material to an elevated temperature above room temperature and performing desired shaping and forming operations while the material is maintained at the elevated temperature. The resulting pre-form material, such as a billet or rod, is then further processed into an intermediate form, such as a rod, wire, tube, sheet or plate product by repetitive cold-forming and annealing cycles. Methods of forming the material may include pressing, extrusion, rolling, drawing, swaging, ECAP, ECAP-conform, high-pressure torsion, severe plastic deformation, forging, pilgering, and the like.

This intermediate material may be made by, for example, a schedule of drawing and annealing to create an initial coarse wire structure ready for final processing. Thereafter, wires 730 or 731 (FIGS. 1-5) may be subjected to a final cold work conditioning step, and possibly a final heat treatment step, in order to impart desired mechanical properties to the finished wire product as further described below.

Figure 2:
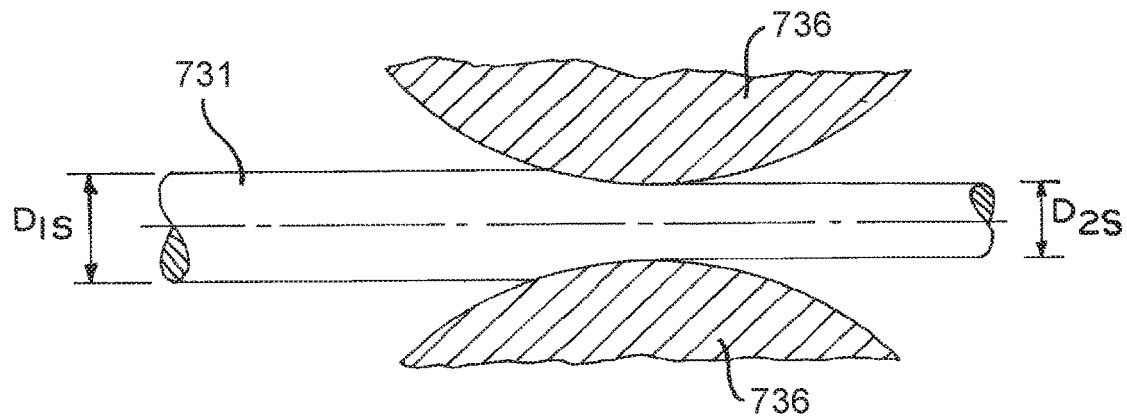
FIG. 2 is a schematic view illustrating an exemplary forming process of monolithic wire using a lubricated drawing die.

In one exemplary embodiment shown in FIG. 2, monolithic wire 731 made of a Mg—Li—Zn—Ca—Mn material (including further alloys thereof, as described herein) may be initially produced using conventional methods, including a schedule of drawing and annealing in order to convert the pre-form material (such as an ingot or rod) into a wire of a desired diameter prior to final processing. That is, the pre-form material is drawn through a die 736 (FIG. 2) to reduce the outer diameter of the intermediate material slightly while also elongating the material, after which the material is annealed to relieve the internal stresses (i.e., retained cold work) imparted to the material by the drawing process. This annealed material is then drawn through a new die 736 with a smaller finish diameter to further reduce the diameter of the material, and to further elongate the material. Further annealing and drawing of the material is iteratively repeated until the material is formed into a wire construct ready for final processing into wire 731.

Figure 3:
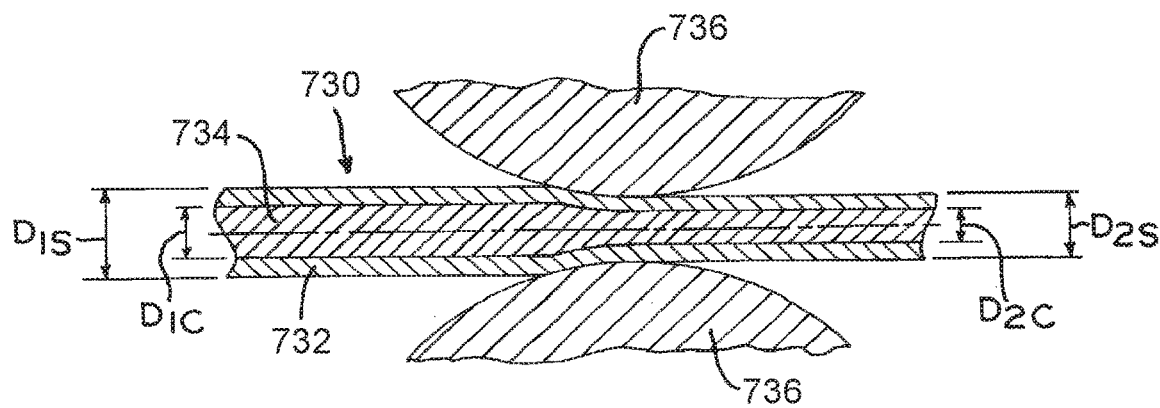
FIG. 3 is a schematic view illustrating an exemplary forming process of composite wire using a lubricated drawing die.

To form composite wire 730 (FIG. 3) such as DFT®, core 734 is inserted within shell 732 to form an intermediate construct, and an end of this intermediate construct is then tapered to facilitate placement of the end into a drawing die 736 (FIG. 3). The end protruding through the drawing die 736 is then gripped and pulled through the die 736 to reduce the diameter of the construct and bring the inner surface of shell 732 into firm physical contact with the outer surface of core 734. More particularly, the initial drawing process reduces the inner diameter of shell 732, such that shell 732 closes upon the outer diameter of core 734 and the inner diameter of shell 732 equals the outer diameter of core 734 whereby, when viewed in section, the inner core 734 will completely fill the outer shell 732 as shown in FIG. 3.

Exemplary composite wires 730 may be formed using a Mg—Li—Zn—Ca—Mn alloy made in accordance with the present disclosure (for shell 732 and another material for core 734). Exemplary materials for core 734 may include Mg and Mg-alloys, Zn and Zn-alloys, Fe and Fe-alloys, non-absorbable alloys, or polymers.

The step of drawing subjects wire 730 or 731 to cold work. For purposes of the present disclosure, cold-working methods effect material deformation at or near room temperature, e.g. 20-30° C. In the case of composite wire 730, drawing imparts cold work to the material of both shell 732 and core 734, with concomitant reduction in the cross-sectional area of both materials. The total cold work imparted to wire 730 or 731 during a drawing step can be characterized by the following formula (I):

$$cw = 1 - \left(\frac{D_2}{D_1}\right)^2 \times 100\% \quad (I)$$

wherein "cw" is cold work defined by reduction of the original material area, "$D_{2S}$" is the outer cross-sectional diameter of the wire after the draw or draws, and "$D_{1S}$" is the outer cross-sectional diameter of the wire prior to the same draw or draws.

Referring to FIGS. 2 and 3, the cold work step may be performed by the illustrated drawing process. As shown, wire 730 or 731 is drawn through a lubricated die 736 having an output diameter $D_{2S}$, which is less than diameter Dis of wire 730 or 731 prior to the drawing step. The outer diameter of wire 730 or 731 is accordingly reduced from pre-drawing diameter Dis to drawn diameter $D_{2S}$, thereby imparting cold work cw.

Alternatively, net cold work may be accumulated in wire 730 or 731 by other processes such as cold-swaging, rolling the wire (e.g., into a flat ribbon or into other shapes), extrusion, bending, flowforming, severe plastic deformation, or pilgering. Cold work may also be imparted by any combination of techniques including the techniques described here, for example, cold-swaging followed by drawing through a lubricated die finished by cold rolling into a ribbon or sheet form or other shaped wire forms. In one exemplary embodiment, the cold work step by which the diameter of wire 730 is reduced from Dis to $D_{2S}$ is performed in a single draw and, in another embodiment, the cold work step by which the diameter of wire 730 is reduced from $D_{1S}$ to $D_{2S}$ is performed in multiple draws which are performed sequentially without any annealing step therebetween. When calculating cold work cw using formula (I) above, it is assumed that no anneal has been performed subsequent to the process of imparting cold work to the material.

For processes where the drawing process is repeated without an intervening anneal on composite wire 730, each subsequent drawing step further reduces the cross section of wire 730 proportionately, such that the ratio of the sectional area of shell 732 and core 734 to the overall sectional area of wire 730 is nominally preserved as the overall sectional area of wire 730 is reduced. Referring to FIG. 3, the ratio of pre-drawing core outer diameter $D_{1C}$ to pre-drawings shell outer diameter Dis is the same as the corresponding ratio post-drawing. Stated another way, $D_{1C}/D_{1S}=D_{2C}/D_{2S}$.

Thermal stress relieving, otherwise known in the art as annealing, at a nominal temperature not exceeding the melting point of the wire material (or, for a composite wire, either the first or second materials), is used to improve the ductility of the fully dense composite between drawing steps, thereby allowing further plastic deformation by subsequent drawing steps. Further details regarding wire drawing are discussed in U.S. Pat. No. 7,989,703, issued Aug. 2, 2011, entitled "Alternating Core Composite Wire", assigned to the assignee of the present invention, the entire disclosure of which is incorporated by reference herein.

Heating wire 730 to a temperature sufficient to cause recrystallization of grains eliminates accumulated cold work. The cold work imparted by each iterative cold work process is relieved by fully annealing the material between draws, thereby enabling the next iterative cold working process. In full annealing, the cold-worked material is heated to a temperature sufficient to substantially fully relieve the internal stresses stored in the material, thereby relieving the stored cold work and "resetting" cold work to zero.

Figure 4:
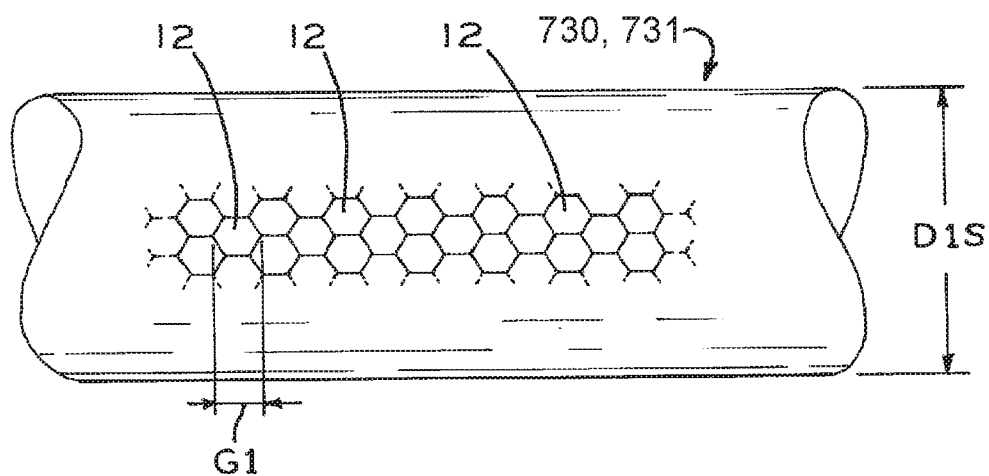
FIG. 4 is an elevation view of a wire in accordance with the present disclosure, before a final cold working process.
Figure 5:
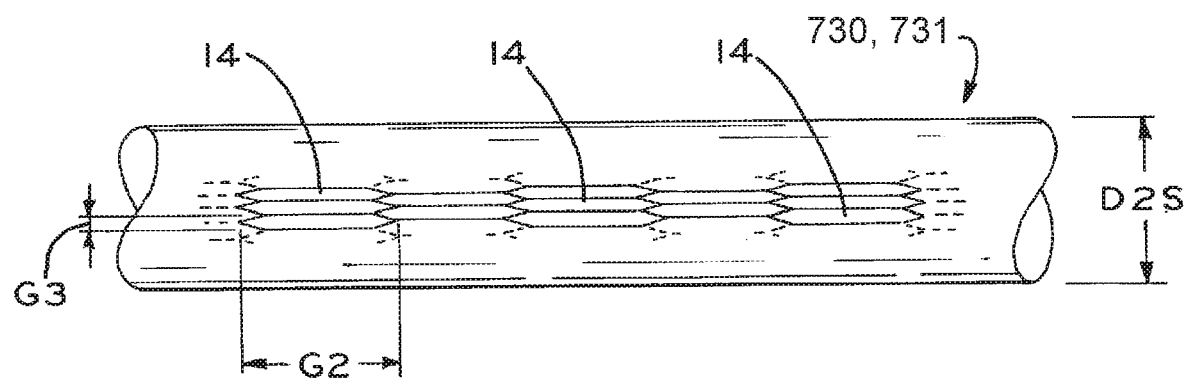
FIG. 5 is an elevation view of the wire of FIG. 4, after the final cold working process.

On the other hand, wires 730 or 731 subject to drawing or other mechanical processing without a subsequent annealing process retain an amount of cold work. The amount of retained work depends upon the overall reduction in diameter from Dis to Des, and may be quantified on the basis of individual grain deformation within the material as a result of the cold work imparted. Referring to FIG. 4, for example, wire 731 is shown in a post-annealing state, with grains 12 shown substantially equiaxed, i.e., grains 12 define generally spheroid shapes in which a measurement of the overall length G1 of grain 12 is substantially the same regardless of the direction of measurement. After drawing wire 731 (as described above), equiaxed grains 12 are converted into elongated grains 14 (FIG. 5), such that grains 14 are longitudinal structures defining an elongated grain length G2 (i.e., the longest dimension defined by grain 14) and a grain width G3 (i.e., the shortest dimension defined by grain 14). The elongation of grains 14 results from the cold working process, with the longitudinal axis of grains 14 generally aligned with the direction of drawing, as illustrated in FIG. 5.

The retained cold work of wire 731 after drawing can be expressed as the ratio of the elongated grain length G2 to the width G3, such that a larger ratio implies a grain which has been "stretched" farther and therefore implies a greater amount of retained cold work. By contrast, annealing wire 731 after an intermediate drawing process recrystallizes the material, converting elongated grains 14 back to equiaxed grains 12 and "resetting" the retained cold work ratio to 1:1 (i.e., no retained cold work).

For the present Mg—Li—Zn—Ca—Mn materials, full annealing may be accomplished at a temperature about 200-350° C. for at least several seconds for thin wire (i.e., having a small cross-sectional area of between 0.000127 sq. mm and 0.5 sq. mm) to tens of minutes for thicker materials (i.e., having a larger cross-sectional area of between 1 sq. mm and 125 sq. mm). Alternatively, a full anneal can be accomplished with a higher temperature, such as between 350° C. and 450° C., for a shorter time, such as between several milliseconds and less than 5 minutes, again depending on cross-sectional area of the material. Of course, a relatively higher temperature annealing process can utilize a relatively shorter time to achieve a full anneal, while a relatively lower temperature will typically utilize a relatively longer time to achieve a full anneal. In addition, annealing parameters can be expected to vary for varying wire diameters, with smaller diameters shortening the time of anneal for a given temperature. Whether a full anneal has been accomplished can be verified in a number of ways as well known in the art, such as microstructural examinations using scanning electron microscopy (SEM), mechanical testing for ductility, strength, elasticity, etc., and other methods. Moreover, the impact of annealing parameters on the precipitation of either $Mg_2Ca$ or $Mg_6Zn_3Ca_2$ intermetallic phases can be considered when designing a manufacturing process for a particular device.

Further discussion of cold working and annealing methods can be found in U.S. Pat. No. 8,840,735, issued Sep. 23, 2014 and entitled FATIGUE DAMAGE RESISTANT WIRE AND METHOD OF PRODUCTION THEREOF, the entire disclosure of which is hereby incorporated by reference.

The resulting coarse wire material may then be finally processed into a final form, such as a fine wire suitable for integration into a stent or other medical device. Exemplary wire constructs are described in further detail below.

5. Wire Properties

As further described in detail below in the Examples, the Mg—Li—Zn—Ca—Mn material of the present disclosure exhibit a combination of high strength and high ductility not found in other combinations of nutrient metals. When alloyed with yttrium, the present Mg—Li—Y—Zn—Ca—Mn material also outperforms other combinations of nutrient metals plus yttrium.

While elongation to fracture is used as a proxy for ductility for wires 730, 731 as discussed herein, elongation to fracture of a material is not necessarily indicative of the functional ductility of the material. Materials with relatively low elongations to failure can have relatively high ductility, when ductility is considered to be ability to withstand high bending strain or significant cold reduction (e.g., via drawing) without fracture.

Mg—Li—Zn—Ca—Mn made in accordance with the present disclosure and having no stored cold work exhibits ductility sufficient to allow at least 10%, 15%, 20%, or 25% elongation before fracture, with high ductility being associated with levels of lithium at the upper end of the range of 1.0-5.0 wt. % and vice-versa. This high ductility allows the material to be substantially cold worked, either as a processing step (followed by annealing) or to strengthen the material for a final construct. Cold work capacity for the present Mg—Li—Zn—Ca—Mn materials may be as much as 60%, 75% or 90%, for example, wherein the cold work capacity is commensurate with ductility. The addition of yttrium may increase ductility, particularly in materials as-annealed (i.e., having no retained cold work) due to a refined grain size and reduced crystallographic texture.

Figure 6A:
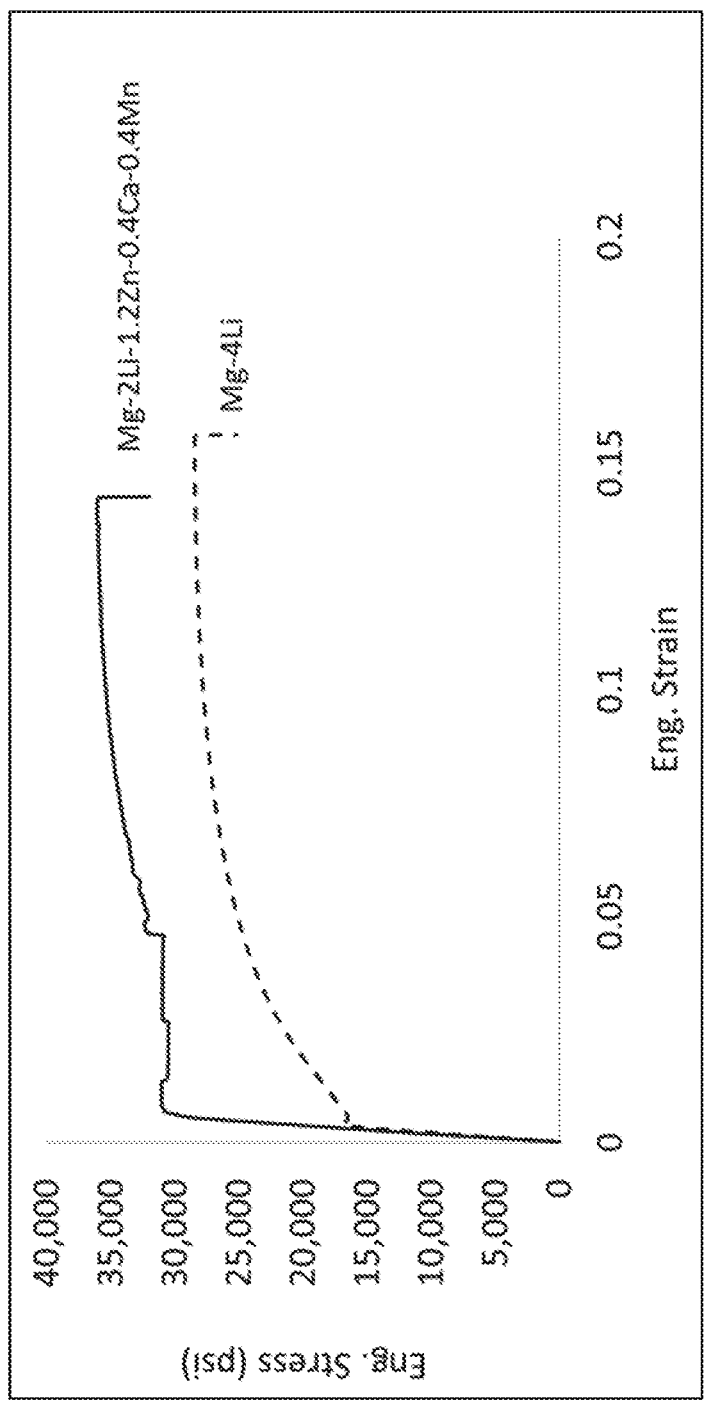
FIG. 6A is a stress-strain graph, drawn to scale, showing a control material juxtaposed against a material made in accordance with the present disclosure.

Mg—Li—Zn—Ca—Mn made in accordance with the present disclosure and having no stored cold work also exhibits high strength, with a potential for higher strength through cold work processing. In the as-annealed condition, the present Mg—Li—Zn—Ca—Mn material exhibits an ultimate strength of at least 25 ksi, 32 ksi or 40 ksi, with higher strength being associated with levels of zinc, calcium and manganese at the upper end of their respective ranges of 0.2-2.0 wt. %, 0.1-0.5 wt. % and 0.1-0.8 wt. %, and vice-versa. For example, FIG. 6A illustrates a stress-strain curve of a Mg-2Li-1.2Zn-0.4Ca-0.4Mn alloy made in accordance with the present disclosure, as further described in the Examples below. As compared to a binary Mg-4Li alloy also shown in FIG. 6A, the present alloy exhibits increases yield strength and ultimate strength. FIG. 6B illustrates additional characteristics of the same Mg-2Li-1.2Zn-0.4Ca-0.4Mn alloy, both before and after cold working, as well as characteristics of a Mg-2Li-2Y-1.2Zn-0.4Mn-0.4Ca alloy, both before and after cold working. FIGS. 6A and 6B are drawn to scale. The nominal strength values of any of the present Mg—Li—Zn—Ca—Mn alloys may be increased by 25%, 50% or 100% by cold work, with greater cold work potential being commensurate with ductility of the material as described above.

Similarly, the present Mg—Li—Zn—Ca—Mn material exhibits a yield strength of at least 20 ksi, 25 ksi or 30 ksi, with a similar commensurate relationship to levels of zinc, calcium and manganese and similar strength increases realized from the addition of yttrium.

Figure 6C:
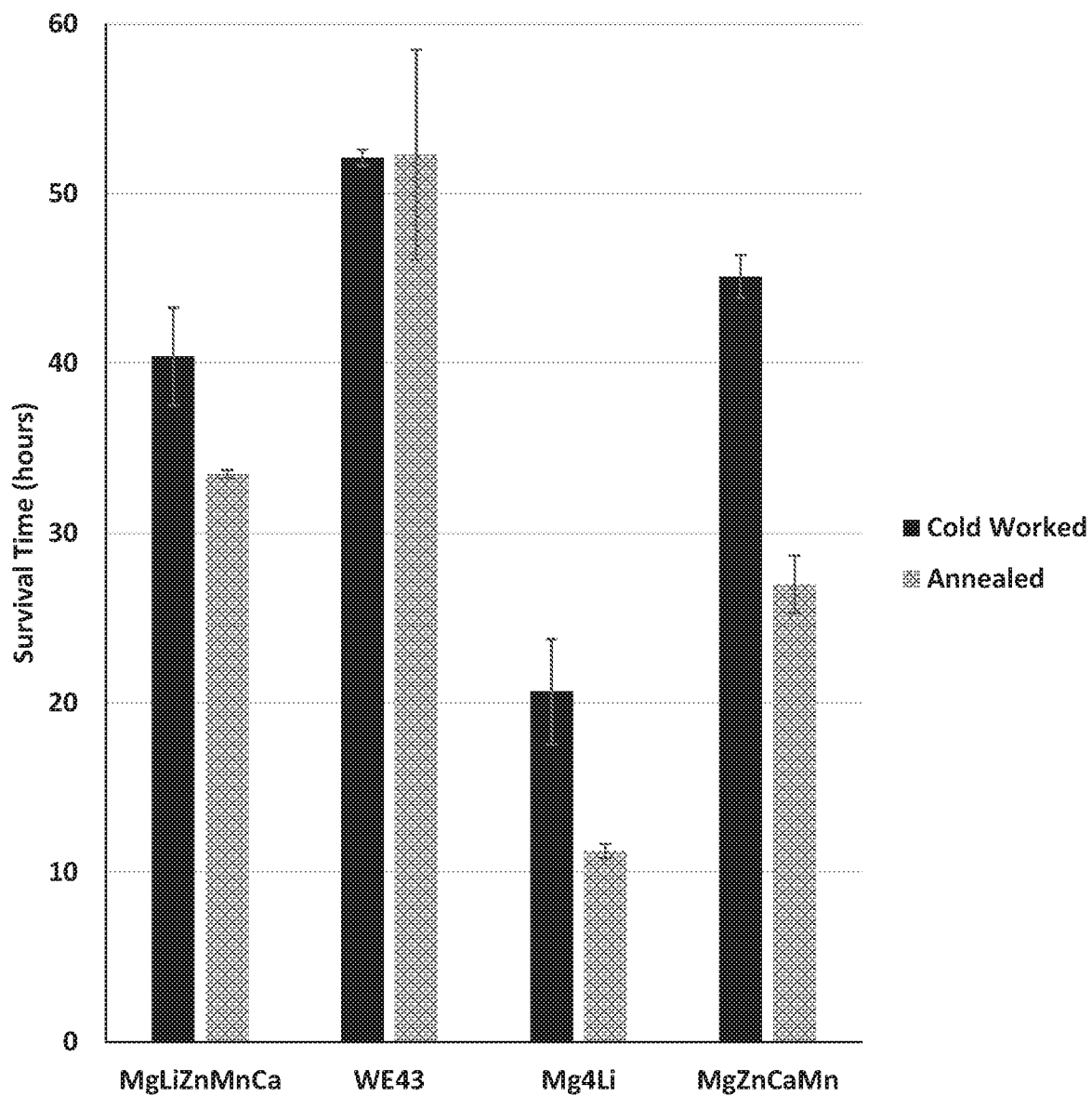
FIG. 6C is a graph, drawn to scale, showing degradation characteristics of material made in accordance with the present disclosure against various control materials.

Turning to FIG. 6C, the present Mg—Li—Zn—Ca—Mn material also demonstrates high in-vivo survivability with a predictably long degradation profile. Its time-to-failure while bearing a load in a corrosive environment (as specifically described in Example 4 below) far exceeds known binary Mg—Li alloys, such as Mg-4Li as shown in FIG. 6C, and is generally commensurate with Mg—Zn—Ca—Mn alloys which lack the benefits of lithium as discussed in herein. While the present Mg—Li—Zn—Ca—Mn material has a time-to-failure somewhat lower than WE43, it may be sufficient for many applications while also offering an improved in-vivo biocompatibility profile as compared to WE43.

In the present alloy constituency ranges discussed herein, time-to-failure of 0.010-inch diameter wires in an as-annealed state can be expected to exhibit a mean survival of at least 30 hours in Hanks' Balanced Salt Solution maintained at 37° C. and 7.4 pH while also being held at an initial stress of 110 MPa. Similarly, time-to-failure of 0.010-inch diameter wires in a cold-worked state having 50% retained cold work can be expected to exhibit a mean survival of at least 30 hours in Hanks' Balanced Salt Solution maintained at 37° C. and 7.4 pH while also being held at an initial stress of 110 MPa. Moreover, any wires made in accordance with the present disclosure and suitable for use in vivo can be expected to exhibit a mean survival of at least 24 hours in typical in vivo conditions (i.e., at body temperature, positioned within the body, and subject to typical stresses associated with medical devices as described herein).

6. Medical Device Applications

A number of medical devices may be made of the present materials, which are beneficial for any device whose function and presence in the body may change and diminish over time. Some exemplary such devices are described below, it being understood that the present materials may also be used in any other suitable medical device application.

Figure 1A:
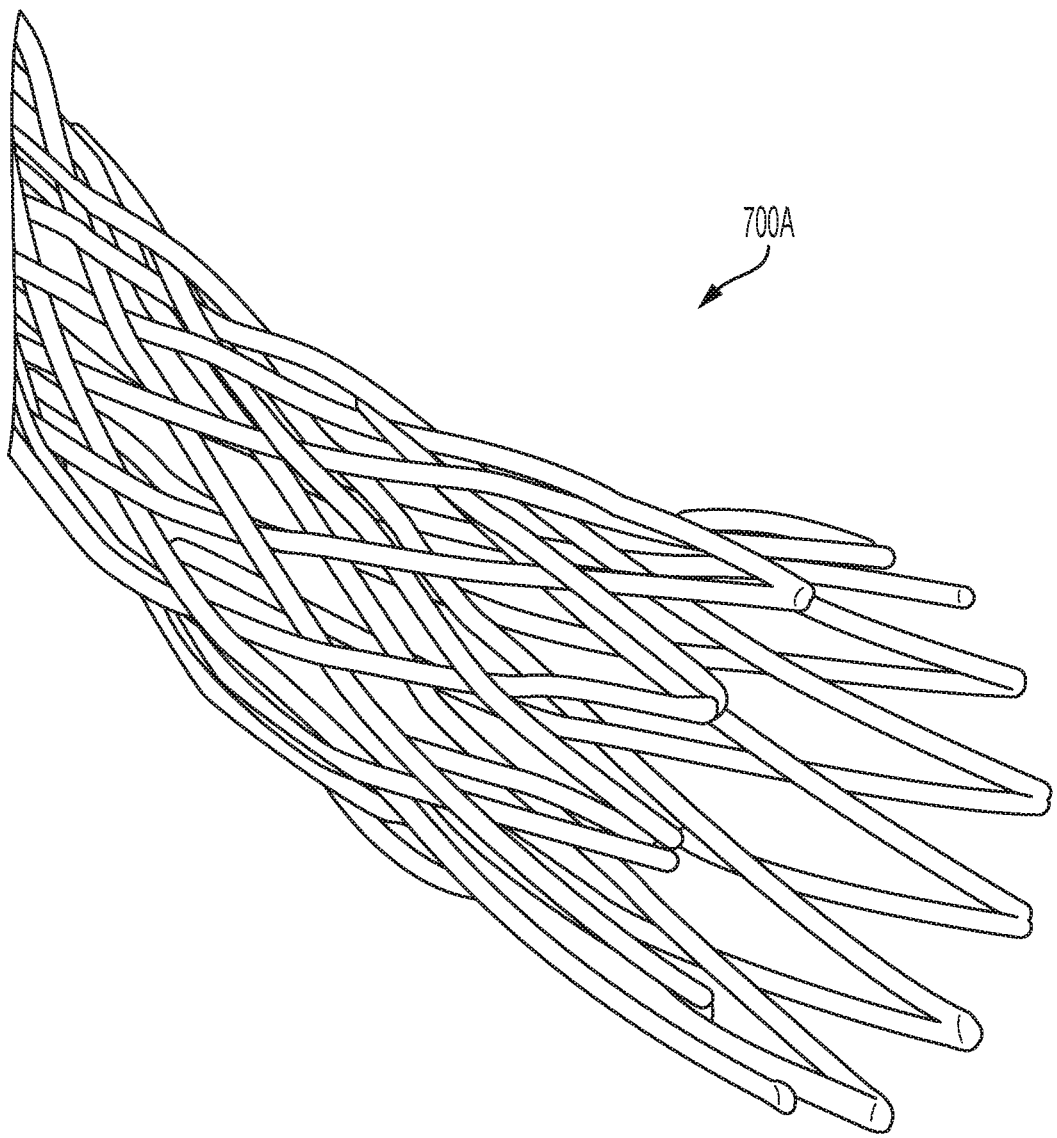
FIG. 1A is a perspective view of another braided stent comprising wire elements formed into a mesh tubular scaffold, in accordance with the present disclosure.
Figure 8:
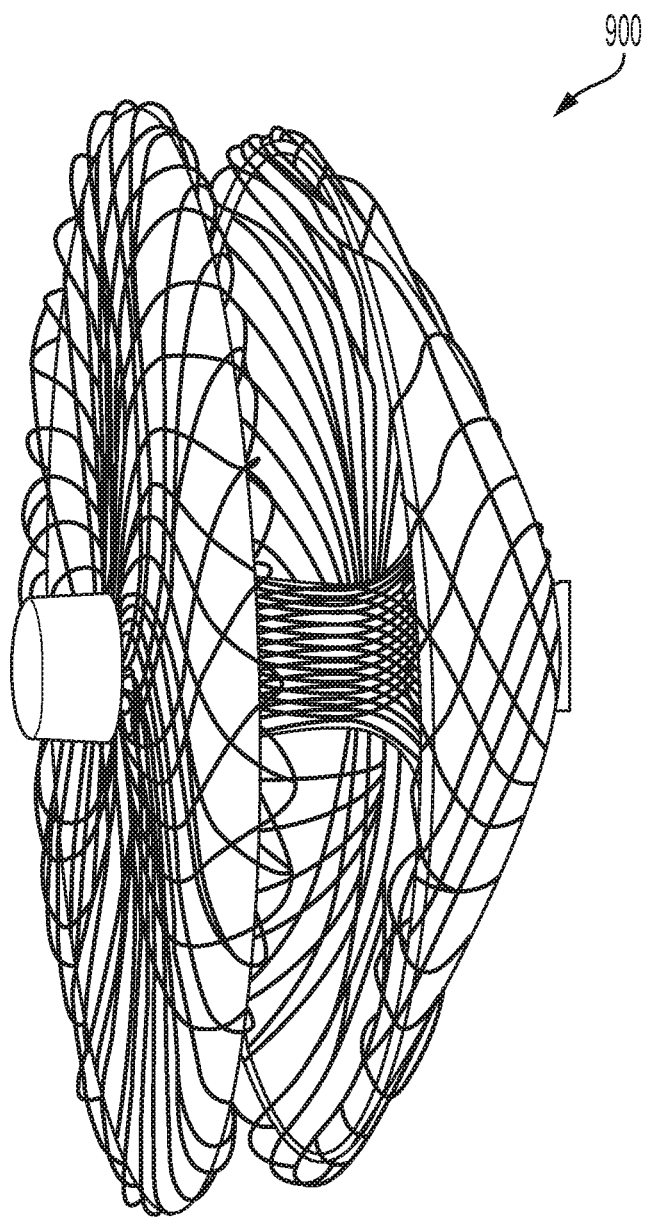
FIG. 8 is a perspective view of a septal occluder designed for use in vivo and incorporating wires in accordance with the present disclosure.

As noted above, wires 730, 731 may be used for vascular devices such as stent 700 (FIG. 1) or 700A (FIG. 1A). Stent 700 may provide a high degree of initial vessel support, and this vessel support may then diminish slowly over time in vivo as wires 730, 731 degrade. Other wire-based vascular devices suitable for use with wires 730, 731 include aneurysm occlusion devices, septal occluders such as occluder 900 (FIG. 8), flow diverters, filters, and grafts.

Figure 7:
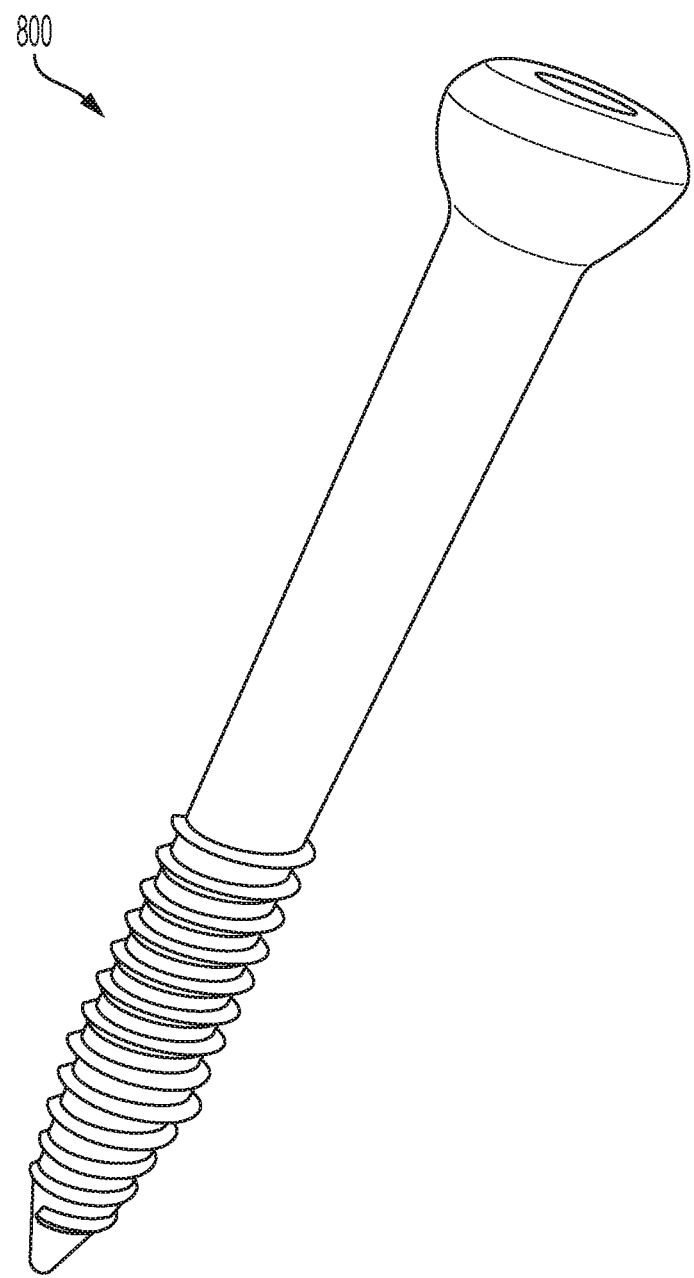
FIG. 7 is a perspective view of a medical screw designed for use in vivo and made from a material in accordance with the present disclosure.

Wires 730, 731, or other constructs, may also be used in orthopedic fixation. Exemplary applications include screws such as screw 800 (FIG. 7), pins, nails, k-wires, and cerclage cables (e.g., for sternal closure), all of which may be implanted at a surgical site to provide a high level of mechanical support to the adjacent tissue, and then may degrade over time as the tissue itself heals.

Still other medical device applications for wires 730, 731 include surgical intervention devices, such as surgical staples, ligation clips, and tacks. These devices may be used to effect a temporary closure of some the relevant part of the anatomy, then to release this closure over time as the device degrades. Still other applications may include devices used in renal therapy, temporary pacing leads, and many other indications.

EXAMPLES

The following non-limiting Examples illustrate various features and characteristics of the present invention, which is not to be construed as limited thereto.

In these Examples, exemplary monolithic Mg—Li—Zn—Ca—Mn and Mg—Li—Y—Zn—Ca—Mn alloy wires in accordance with the present disclosure were produced, tested and characterized, particularly with regard to material workability and mechanical strength.

The Examples below demonstrate that for absorbable wire applications requiring high ductility, such as staples, ligation, and stents, the present MgLiZnMnCa alloy has an optimal combination of strength, ductility, corrosion resistance, and biocompatibility.

Mechanical performance was evaluated for each wire sample via a uniaxial tensile test on an Instron Model 5565 test machine available from Instron of Norwood, Massachusetts, USA). More specifically, destructive uniaxial tension testing of the wire materials was used to quantify the ultimate strength, yield strength, axial stiffness and ductility of candidate materials, using methods described in *Structure-Property Relationships in Conventional and Nanocrystalline NiTi Intermetallic Alloy Wire, Journal of Materials Engineering and Performance* 18, 582-587 (2009) by Jeremy E. Schaffer, the entire disclosure of which is hereby expressly incorporated herein by reference. These tests are run using servo-controlled Instron load frames in accordance with industry standards for the tension testing of metallic materials.

For rotary beam fatigue testing in accordance with the Examples herein, a wire sample is cut to a length of approximately about 118 mm (e.g., for a 0.33 mm diameter wire), then secured at its axial ends to rotatable jaws. The free portion of the wire between the jaws is bent to introduce a desired tensile strain at the "peak" or outermost portion of the bend. Directly opposite this peak of the bend, the wire experiences a compressive strain equal to the tensile strain, with the nominal value of both the tensile and compressive strains referred to herein as the "strain amplitude." The jaws are then rotated in concert (i.e., each jaw rotated with the same speed and in the same direction), such that the area of maximum tensile strain is rotated around the wire "peak" and transitioned to the area of maximum compressive strain with each 180-degree rotation of the jaws and wire. Rotary beam fatigue testing is further described in ASTM E2948-14, the entire disclosure of which is hereby expressly incorporated herein by reference.

Example 1

A Mg—Li—Zn—Mn—Ca alloy of the present disclosure was produced having 2 wt. % Li, 1.2 wt. % Zn, 0.4 wt. % Mn and 0.4 wt. % Ca, with the balance magnesium and unavoidable impurities. This alloy was first made into an ingot by vacuum induction melting the material constituents and then casting the material into a 2" mold.

The ingot was then hot worked by extrusion to a 0.5-inch diameter at a temperature of 325° C., using a ram speed of 10 inches per minute. The extruded rod was then centerless ground and processed into a monolithic round wire via a series of cold draws through standard wire-drawing practices, as described above, to a final diameter of 0.0079 inches.

The wire was then fully annealed as described above to produce a first final wire construct, which was subjected to uniaxial tensile testing as described above. The wire demonstrated an ultimate tensile strength of 37 ksi and a yield strength of 30 ksi. The wire was capable of 14% elongation prior to failure. These results are illustrated in FIG. 6B as line "A," which is the lower dashed line.

Another sample of the monolithic wire was further cold drawn to a final diameter of 0.005 inches and not annealed, producing a second final wire construct having 75% retained cold work. This wire was subject to the same uniaxial tensile testing as the first final wire construct and demonstrated an ultimate tensile strength of 64 ksi and a yield strength of 56 ksi. The wire was capable of 7% elongation prior to failure. These results are illustrated in FIG. 6B as line "B," which is the upper solid line.

Example 2

A Mg—Li—Y—Zn—Mn—Ca alloy of the present disclosure was produced having 2 wt. % Li, 2 wt. % Y, 1.2 wt. % Zn, 0.4 wt. % Mn and 0.4 wt. % Ca, with the balance magnesium and unavoidable impurities. Therefore, this alloy has the same chemistry as the alloy in Example 1 above, but further includes 2 wt. % yttrium. This alloy was first made into an ingot by vacuum induction melting the material constituents and then casting the material into a 2" mold.

The ingot was then hot worked by extrusion to a 0.5-inch diameter at a temperature of 325° C., using a ram speed of 10 inches per minute. The extruded rod was then processed into a monolithic round wire via a series of cold draws and anneals through standard wire-drawing practices, as described above, to a final diameter of 0.0099 inches.

The Mg—Li—Y—Zn—Mn—Ca material of the present example proved to have reduced ductility and workability as compared to the Mg—Li—Zn—Mn—Ca material of Example 1, requiring additional anneals to achieve a given diameter reduction. However, it required fewer anneals for a given diameter reduction when compared to other magnesium alloys like WE43 or Mg—Zn—Ca.

The wire was then fully annealed as described above to produce a first final wire construct, which was subjected to uniaxial tensile testing as described above. The wire demonstrated an ultimate tensile strength of 39 ksi and a yield strength of 33 ksi. The wire was capable of 19% elongation prior to failure. These results are illustrated in FIG. 6B as line "C," which is the upper dashed line. Thus, as compared to the annealed Mg—Li—Zn—Mn—Ca material described above in Example 1, it can be seen that the addition of yttrium increased both strength and ductility in the annealed state (i.e., with no retained cold work).

Another sample of the monolithic wire was further cold drawn to a final diameter of 0.005 inches and not annealed, producing a second final wire construct having 75% retained cold work. This wire was subject to the same uniaxial tensile testing as the first final wire construct, and demonstrated an ultimate tensile strength of 61 ksi and a yield strength of 45 ksi. The wire was capable of 9% elongation prior to failure. These results are illustrated in FIG. 6B as line "D," which is the lower solid line. Thus, as compared to the cold worked Mg—Li—Zn—Mn—Ca material described above in Example 1, it can be seen that the addition of yttrium did not increase strength but did increase ductility.

Example 3

A conventional Mg—Li alloy was produced having 4 wt. % Li, with the balance magnesium and unavoidable impurities. This alloy was first made into an ingot by vacuum induction melting the material constituents and then casting the material into a 2" mold.

The ingot was then hot worked by extrusion to a 0.5-inch diameter at a temperature of 300° C., using a ram speed of 10 inches per minute. The extruded rod was then processed into a monolithic round wire via a series of cold draws and anneals through standard wire-drawing practices, as described above, to a final diameter of 0.0079 inches.

As shown by the dashed line in FIG. 6A, the conventional Mg—Li material of the present example proved to have equivalent or increased ductility and workability as compared to the materials of Example 1, requiring equivalent or fewer anneals to achieve a given diameter reduction. However, the strength of the alloy was very low by comparison to the materials described in Example 1, as shown in FIGS. 6A and 6B.

The wire was then fully annealed as described above to produce a first final wire construct, which was subjected to uniaxial tensile testing as described above. The wire demonstrated an ultimate tensile strength of 28 ksi and a yield strength of 17 ksi. The wire was capable of 16% elongation prior to failure.

Thus, as compared to the annealed Mg—Li—Zn—Mn—Ca material described above in Example 1 or the Mg—Li—Y—Zn—Mn—Ca material described in Example 2, it can be seen that the additions of Zn, Mn, Ca, and optionally Y produce increased annealed yield strength of between 76% to 94% while retaining good ductility.

Example 4

To assess the corrosion behavior of the inventive alloy in comparison to other known alloys, the following experiment was conducted. Wires having a finished diameter of 0.010 inches were produced from four different alloys:
  Mg-2Li-1.2Zn-0.4Mn-0.4Ca, in accordance with the present disclosure and also discussed above in Examples 1 and 2;
  Mg-1Zn-0.3Ca-0.1Mn, as a control sample for a similar nutrient metal alloy without lithium;
  Conventional WE43, as a control sample for a rare-earth containing alloy; and
  Conventional Mg-4Li, as a control sample, also discussed above in Example 3.

Each of the four wires was produced as an annealed wire (i.e., with no retained cold work) and a cold worked wire (i.e., with retained a cold work of 45-75%), for a total of eight individual alloy/condition combinations. At least two samples of each alloy/condition combination were tested as described below. For the cold-worked wires, the WE43 wire had 75% retained cold work, Mg-1Zn-0.3Ca-0.1Mn had 50% retained cold work, Mg-2Li-1.2Zn-0.4Mn-0.4Ca had 50% retained cold work, and MgLi had 45% retained cold work. These cold work levels were designed to achieve mechanical properties for each wire typically desired for medical device applications.

Each wire sample was subjected to corrosion in Hanks' Balanced Salt Solution (HBSS) maintained at 37° C. and 7.4 pH while also being held at an initial stress of 16 ksi (110 MPa) via a dead-weight. HBSS is a physiologically relevant inorganic salt solution which is considered to be an adequate Mg corrosion medium for in vitro tests. HBSS is commercially available and can be purchased from MilliporeSigma (formerly Sigma Aldrich) of St. Louis, Missouri, United States. For the present Example, this commercially available HBSS was modified with 1.6 g/L sodium bicarbonate and 0.265 g/L of calcium chloride, also commercially available and purchased from Sigma Alrdrich.

The time to wire fracture was measured for each sample, providing a measure of relative corrosion resistance.

The results of the experiment are shown in FIG. 6C. The present MgLiZnMnCa alloy exhibited a mean survival of at least 40 hours in the cold-worked form and at least 33 hours in the as-annealed form. As expected, this time-to-failure is less than the rare-earth containing WE43, which had a mean survival time in excess of 50 hours in both cold-worked and annealed forms. However, the survival of the MgLiZnMnCa alloy was substantially longer than the Mg4Li binary alloy, which failed after about 20 hours and 11 hours in the cold-worked and annealed forms respectively. This suggests a much longer survival in-vivo for the present alloys as compared to baseline binary alloys.

When comparing the present MgLiZnMnCa alloy to the conventional MgZnCaMn alloy, the survival time in the cold-worked condition was only slightly reduced by the Li addition, from about 45 hours for the MgZnCaMn alloy versus the aforementioned time of about 40 hours for the present MgLiZnMnCa alloy. Surprisingly, the survival time in the annealed condition was longer in the MgLiZnMnCa alloy (about 33 hours) than the MgZnCaMn alloy (about 28 hours), which would not be expected due to the greater reactivity of the Li. Thus, the present MgLiZnMnCa alloys exhibit in-vivo survival times better than or commensurate with similarly biocompatible alloys, while also showing superior strength and ductility.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An alloy for use in an absorbable medical device, the alloy comprising:
  between 1.0-5.0 wt. % lithium;
  between 0.2-2.0 wt. % zinc;
  between 0.1-0.5 wt. % calcium;
  between 0.1-0.8 wt. % manganese; and
  balance magnesium and inevitable impurities.

2. The alloy of claim 1, wherein the alloy has no retained cold work and exhibits an ultimate tensile strength reaching 34 ksi.

3. The alloy of claim 1, wherein the alloy has 75% retained cold work and exhibits an ultimate tensile strength reaching 64 ksi.

4. The alloy of claim 1, wherein the alloy has no retained cold work and exhibits a yield strength reaching 26 ksi.

5. The alloy of claim 1, wherein the alloy has 75% retained cold work and exhibits a yield strength reaching 56 ksi.

6. The alloy of claim 1, wherein the alloy has no retained cold work and exhibits a ductility sufficient to allow elongation of 14% before rupture.

7. The alloy of claim 1, wherein the alloy has 75% retained cold work and exhibits a ductility sufficient to allow elongation of 7% before rupture.

8. The alloy of claim 1, wherein the alloy has no retained cold work and exhibits a mean survival of at least 30 hours in Hanks' Balanced Salt Solution maintained at 37° C. and 7.4 pH while also being held at an initial stress of 110 MPa.

9. The alloy of claim 1, wherein the alloy has at least 50% retained cold work and exhibits a mean survival of at least 30 hours in Hanks' Balanced Salt Solution maintained at 37° C. and 7.4 pH while also being held at an initial stress of 110 MPa.

10. The alloy of claim 1, wherein the alloy has no retained cold work and exhibits:
   an ultimate tensile strength reaching 34 ksi;
   a yield strength reaching 26 ksi;
   a ductility sufficient to allow elongation of 14% before rupture; and
   a mean survival of at least 30 hours in Hanks' Balanced Salt Solution maintained at 37° C. and 7.4 pH while also being held at an initial stress of 110 MPa.

11. The alloy of claim 1, wherein the alloy has at least 50% retained cold work and exhibits:
   an ultimate tensile strength reaching 64 ksi;
   a yield strength reaching 56 ksi;
   a ductility sufficient to allow elongation of 7% before rupture; and
   a mean survival of at least 30 hours in Hanks' Balanced Salt Solution maintained at 37° C. and 7.4 pH while also being held at an initial stress of 110 MPa.

12. The alloy of claim 1, further comprising yttrium in an amount up to 2.5 wt. %.

13. The alloy of claim 12, wherein the alloy has no retained cold work and exhibits an ultimate tensile strength reaching 39 ksi.

14. The alloy of claim 12, wherein the alloy has 75% retained cold work and exhibits an ultimate tensile strength reaching 61 ksi.

15. The alloy of claim 12, wherein the alloy has no retained cold work and exhibits a yield strength reaching 33 ksi.

16. The alloy of claim 12, wherein the alloy has 75% retained cold work and exhibits a yield strength reaching 45 ksi.

17. The alloy of claim 12, wherein the alloy has no retained cold work and exhibits a ductility sufficient to allow elongation of 19% before rupture.

18. The alloy of claim 12, wherein the alloy has 75% retained cold work and exhibits a ductility sufficient to allow elongation of 10% before rupture.

19. A wire formed from the alloy of claim 1.

20. A medical device formed from an alloy comprising:
   between 1.0-5.0 wt. % lithium;
   between 0.2-2.0 wt. % zinc;
   between 0.1-0.5 wt. % calcium;
   between 0.1-0.8 wt. % manganese; and
   balance magnesium and inevitable impurities.

21. The medical device of claim 20, wherein the medical device is a vascular device.

22. The medical device of claim 20, wherein the medical device is an orthopedic fixation device.

23. The medical device of claim 20, wherein the medical device is a surgical intervention device.

* * * * *